United States Patent [19]

Yoshida

[11] 4,428,673
[45] Jan. 31, 1984

[54] LIGHT DIFFUSION DEVICE

[75] Inventor: Hajime Yoshida, Tokyo, Japan

[73] Assignee: Hajime Industries Ltd., Japan

[21] Appl. No.: 264,282

[22] Filed: May 18, 1981

[30] Foreign Application Priority Data

Jun. 26, 1980 [JP] Japan ................... 55-87105

[51] Int. Cl.³ ........................................... G01N 21/00
[52] U.S. Cl. ................................ 356/240; 250/223 B;
362/355
[58] Field of Search ............... 356/240; 350/167, 260,
350/431, 321, 3.81, 3.82; 250/223 B; 362/300,
307, 311, 355

[56] References Cited

U.S. PATENT DOCUMENTS

| 2,265,037 | 12/1941 | Gulliksen | 356/240 |
| 2,589,014 | 3/1952 | McLeod | 350/431 X |
| 2,877,342 | 3/1959 | Beach | 350/431 X |
| 3,578,837 | 5/1971 | Brooks | 350/3.81 |
| 4,076,978 | 2/1978 | Brennan et al. | 350/167 X |

FOREIGN PATENT DOCUMENTS 1566553  5/1980  United Kingdom ............... 350/431

Primary Examiner—William L. Sikes
Assistant Examiner—Matthew W. Koren

[57] ABSTRACT

A light diffusion device has a plurality of rough surfaces with different roughnesses which are placed at a light source side of an object to be inspected. The plurality of rough surfaces consecutively diffuse the light emitted from the light source. The diffused light then passes the inspection zone of the object to which a photosensing means is faced from the opposite side to the light source, into which the diffused light is introduced from the light diffusion device after passing the inspection zone of the object.

13 Claims, 7 Drawing Figures

LIGHT DIFFUSION DEVICE

BACKGROUND OF THE INVENTION

1. Field of the Invention

The present invention relates generally to a light diffusion device that is used for inspecting bottle bottoms or the like as an example, and is directed more particularly to a light diffusion device of a simple construction that is suitable for applications to inspect for flaws, dirt and/or foreign material in bottle bottoms.

2. Description of the Prior Art

At bottling production lines, it is generally necessary to have a process between the bottle washing machines and bottle fill or loading machines to inspect for flaws, dirt or mixtures of foreign particles inside the bottles, etc. Such inspection has conventionally depended upon human visual inspection in most cases. Such visual inspection of empty bottles causes eye fatigue in the worker when conducted for long hours (which is the normal case). Eye fatigue increases inspection misses while at the same time such visual inspection limits processing capacity to the human capabilities and high speed inspection is not feasible.

Automatic empty bottle inspection machines are proposed utilizing photo electric conversion means which attempt to overcome such visual inspection defects. An example of such conventional empty bottle inspection machines that use such photo electric conversion means will be explained hereunder in reference with FIG. 1 and FIGS. 2A, 2A' as well as FIGS. 2B and 2B'.

On FIG. 1, 1 is a photo electric conversion means such as photo electric conversion element like a CdS or a video camera, by which the inspected range such as bottom 3 of a bottle 2 or the like to be inspected object is photo sensed, so that it senses flaws, dirt or foreign material on the inside of bottle bottom 3 as a contrast of light and delivers an output as an electrical signal. Changes in the electric output are detected by detection means although not shown on the drawings in order to discriminate flaws, dirt or foreign material on the inside of the bottle bottom 3. On FIG. 1, 4 is a light source which is included a parabolic reflector $4_1$ and a lamp $4_2$ positioned at the focal point of the reflector $4_1$ and which is located at the opposite side of the bottle bottom 3 from the photosensing means and in the example on the drawing is located under the bottle bottom 3. Further, a light diffusing means 5 which is formed of a nontransparent or milky white board to equalize the light from the light source 4 is placed between the light source 4 and bottle bottom 3, by which the light from the light source 4 irradiates the bottle bottom 3 as a uniform or homogenous light.

In this case, the flaws and dirt or the size of foreign particle at the bottle bottom 3 that may be detected can be selected by the brightness of the light source 4 or the sensitivity adjustment of the photo electric conversion means 1 to discriminate very small foreign particles or the like. However, the detection precision is naturally influenced by the structure of the inspected area which is the bottle bottom 3.

In other words, on inspected objects such as bottle 2, it is common that outside protuberances are arranged during the manufacturing process including lines such as line 6 which are generally called baffle marks as shown on FIGS. 2A and 2A', or tear drop like projections which are called knurlings 7 as shown on FIGS. 2B and 2B' or lot numbers or characters or the kind though not shown. Therefore, if the detection sensitivity is raised with consideration only to flaw or dirt detection, the above mentioned protrusions of baffle marks 6 or knurlings 7, etc. will also be detected as light contrasts, in other words, discriminated as an abnormality and it becomes impossible to accurately detect only the flaws, dirt or the like. Accordingly, it is necessary to adjust the detection sensitivity of the system to only detect the flaws, dirt or the like as contrasts of light without detecting the light contrast caused by baffle marks or the like which are unrelated to flaws, dirt or the like.

Actually, in case the detection sensitivity is limited as above described, it naturally causes a reduction in the detection sensitivity of flaws, dirt or the like which should be detected. Therefore, in order to circumvent the reduction of the detection sensitivity without detecting the unnecessary knurlings or the like, conventional detection means have included dipping the outer surface of the bottle bottom 3 into a clear fluid in order to reduce the light refraction at the outside surface of the bottle bottom 3, so that the light contrast of the formed knurling or the like on the outer surface of bottle bottom 3 may be reduced.

However, when bottles that are consecutively moving on conveyor belts or the like are to be automatically inspected, it is extremely difficult task to dip each bottle bottom in such fluid as above mentioned.

OBJECTS AND SUMMARY OF THE INVENTION

Accordingly, it is an object of the present invention to provide a light diffusion device that will allow light contrast formation by, for example, flaws, dirt or foreign particles on the inside surface of a bottle bottom but will avoid light contrast formation owing to protruberances on the outer surface of the bottle bottom such as knurling or the like.

According to an aspect of the present invention, there is provided a light diffusion device for use with an apparatus optically inspecting an object which comprises: a plurality of light diffusing surfaces formed on surfaces of at least one transparent plate, said transparent plate being located between a light source and an object to be inspected, light diffusing degree of said plurality of light diffusing surfaces being selected different with one another so that light emitted from said light source is diffused successively by said plurality of light diffusing surfaces with different diffusion degrees and impinged on said object.

Additional, and other objects, features and advantages of the present invention will become apparent from the following description taken in conjunction with the accompanying drawings in which like references designate the same elements and parts.

DESCRIPTION OF THE PREFERRED EMBODIMENTS

The present invention will be hereinafter described with reference to the attached drawings.

Figure 3:
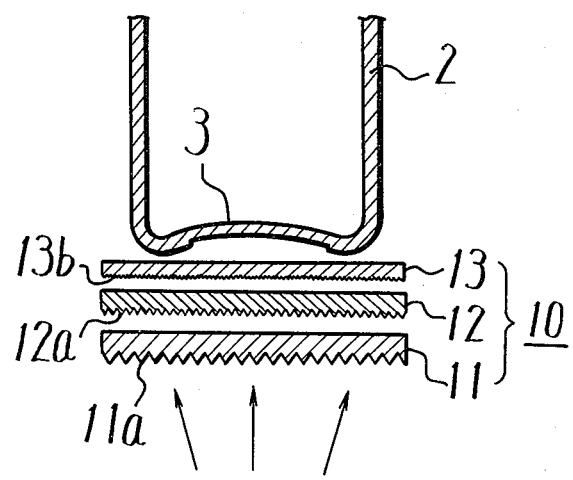
FIG. 3 is a cross-sectional view showing an example of the light diffusion device according to an embodiment of the present invention.
Figure 3:
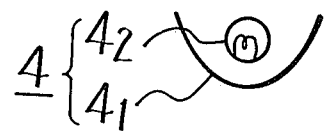

FIG. 3 illustrates in cross-section an embodiment of a light diffusion device according to the present invention. In this example, a light diffusion device 10 consists of three sheets of light diffuser boards 11, 12 and 13 which are each formed of transparent plastic, glass, resin or the like material and respectively have on one side surface light diffuser or diffusing surfaces 11a, 12a and 13a having different degrees of light diffusion.

Figure 1:
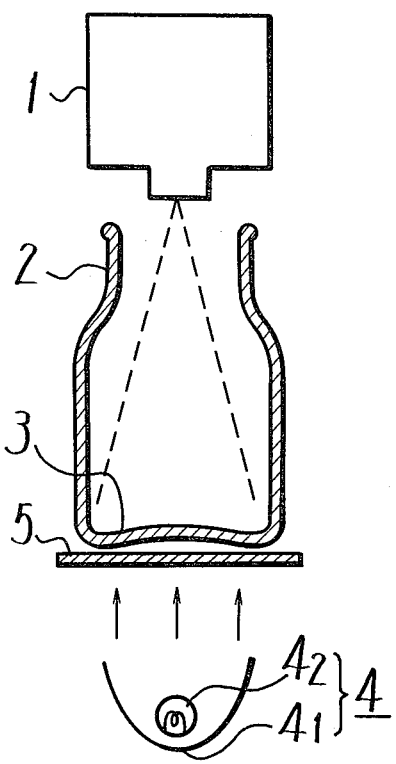
FIG. 1 is a schematic diagram of a conventional empty bottle inspection machine.
Figure 2A:
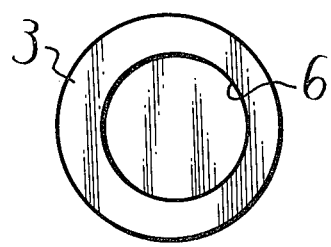
FIGS. 2A and 2A' respectively illustrates the top and side cross-sectional views of a bottle bottom.
Figure 2B:
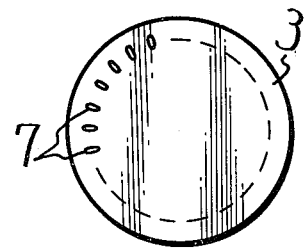
FIGS. 2B and 2B' are the top and side cross-sectional views of another type bottle bottom.
Figure 2A:
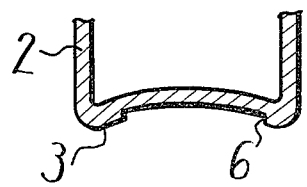
Figure 2B:
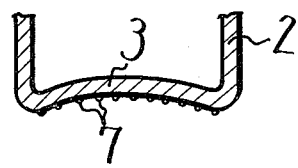

When this light diffusion device 10 is used for the inspection of flaws, dirt or foreign particle mixture on the inside of the bottle bottoms as an example, it is placed between the light source 4 and bottle bottom 3 in the same manner as the conventional methods shown on FIG. 1 and inspection is also conducted in the same manner as the conventional methods by the photo electric conversion means that is placed above the mouth of the bottle 2 (refer to FIG. 1).

Now, according to the example of the present invention shown on FIG. 3, the light diffusing surfaces 11a, 12a and 13a of respective diffuser plates 11, 12 and 13 of the light diffusion device 10, which is placed between the light source 4 and bottle bottom 3, each include a rough surface formed by unevenness on one side surface of each facing the diffuser plates 11, 12 and 13 at the side of light source 4. In this example on FIG. 3, the roughness of each of the light diffuser surfaces 11a, 12a and 13a is arranged to be finer as they are closer to the bottle bottom 3 and further from the light source 4. Accordingly, the approximately parallel light beams emitted from the light source 4 are roughly diffused first by rough surface 11a of light diffuser board 11 through which they pass, and then at the next step pass the rough surface 12a of light diffuser board 12 which has finer roughness than that of the rough surface 11a of diffuser board 11, to be more finely diffused and pass the plate 12 and then enter rough surface 13a of light diffuser board 13, which has even finer roughness than the roughness of rough surface 12a of light diffuser board 12, to be more finely diffused and then pass light diffuser board 13 and go through the bottle bottom 3 by irradiation from the outside of bottle bottom 3 to arrive at the photosensing means (refer to FIG. 1).

As such, the light that passes the light diffusion device 10 and irradiates on the bottle bottom 3 ultimately, is hardly influenced by the light contrast of the preceding rough surface and can minimize the light contrasts of knurlings, baffle marks, characters or the like formed on the outside surface of the bottle bottoms 3 and can transmit only the light contrasts of flaws, dirt or foreign particles inside the bottle bottom 3 to the photosenser means. Therefore, the light diffusion device 10 of the present invention not only increases the detection accuracy but also greatly improves the sensitivity of detection at the photosensing means, which was ascertained through many experimentations and tests.

Further, the formation of the rough surface on each light diffuser board may be any shape such as conical shape, pyramid shape, frustoconical shape or flat head pyramid shape, for instance, with orderly arrangement or at random, in essence, can be of any shape or arrangement that will accomplish the purpose to minimize or suppress the light contrast produced by protrusions on the outside surface of bottle bottom such as knurlings or the like.

It is also apparent that the number of the light diffuser plates that possess rough surfaces to construe the light diffusion device 10 may not necessarily be limited as per the example illustrated on FIG. 3, which may be increased or decreased as necessary.

Figure 4:
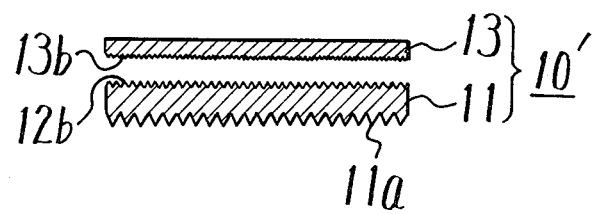
FIG. 4 illustrates in a cross section another embodiment of the present invention.

FIG. 4 illustrates another example 10' of the present invention in which case the light diffuser board 12 in the middle on the example of FIG. 3 is omitted, but the rough surface 12a thereof is formed on the back side surface of rough surface 11a of light diffuser board 11 which is the first stage. It is apparent that the light diffusion device 10' of the invention shown on FIG. 4 may provide exactly the same effects as the example on FIG. 3.

Further, the sequence of roughness arrangements may not necessarily be limited to the illustrated examples.

Further, although the above explains some examples of occasions that the present invention is applied to the detection of flaws, dirt, etc. on the bottle bottom when such bottles have protrusions on the outside surface of the bottle bottoms such as knurlings or marks or the like, the present invention need not be limited to such above described applications and may be applied to other cases where light diffusion is required.

It is further apparent that while the light diffuser boards of the present invention as illustrated in the examples are arranged to be spaced apart from each other, they, of course, may be placed together in contact with each other.

It will be apparent that may modifications and variations could be effected by one skilled in the art without departing from the spirits or scope of the novel concepts of the present invention, so that the spirit or scope of the invention should be determined by the appended claims only.

I claim as my invention:

1. A light diffusion device for interposition between a light source and a transparent object comprising:
   at least one light transmitting plate;
   first and second rough surfaces on said at least one light transmitting plate;
   light from said light source passing progressively through said first rough surface and then through said second rough surface toward said object;
   said first rough surface being effective for producing a first degree of light diffusion;
   said second rough surface being effective for producing a second degree of light diffusion; and
   a roughness of said second rough surface being substantially finer than a roughness of said first rough surface whereby said second degree of light diffusion is substantially greater than said first degree of light diffusion and rough surfaces on said object are thereby prevented from interfering with an inspection of said object.

2. A light diffusion device as claimed in claim 1, wherein said at least one light transmitting plate includes at least first and second parallel transparent plates, said first and second rough surfaces being formed on a surface of said first and second plate respectively which face said light source.

3. A light diffusion device as claimed in claim 2, wherein each of said first and second transparent plates includes said first and second rough surfaces integrally formed thereon.

4. A light diffusion device as claimed in claim 1, wherein said at least one light transmitting plate further includes a second and a third parallel transparent plate, said first, second and third transparent plates including first, second and third rough surfaces respectively on sides of said first, second and third transparent plates, a roughness of said first, second and third rough surfaces being progressively finer nearer said object.

5. A light diffusion device as claimed in claim 4, wherein said first, second and third rough surfaces are integrally formed on one surface of said first, second and third transparent plates.

6. A light diffusion device as claimed in claim 1, wherein said at least one light transmitting plate includes at least first and second light transmitting plates, said first and second rough surfaces being on opposed surfaces of said first light transmitting plate and third rough surface on a third surface of said second light transmitting plate for producing a third degree of light diffusion different from said first and second degrees a fineness of roughnesses of said first, second and third rough surfaces progressively increasing toward said object.

7. A light diffusion device as claimed in claim 1, wherein said at least first and second rough surfaces include first and second rough surfaces on opposed surfaces of a first transparent plate and a third rough surface on one surface of a second transparent plate.

8. A light diffusion device as claimed in claim 1, wherein said first and second rough surfaces include a plurality of conical-shaped projections.

9. A light diffusion device as claimed in claim 1, wherein said first and second rough surfaces include a plurality of pyramid-shaped projections.

10. A light diffusion device as claimed in claim 1, wherein said first and second rough surfaces include a plurality of frustoconical shaped projections.

11. A light diffusion device as claimed in claim 1, wherein said first and second rough surfaces each include a plurality of conical-shaped projections.

12. A light diffusion device as claimed in claim 1, wherein said first and second rough surfaces each include a plurality of pyramid-shaped projections.

13. A light diffusion device as claimed in claim 1, wherein said first and second rough surfaces each include a plurality of frustoconical shaped projections.

* * * * *